United States Patent [19]
Halm et al.

[11] Patent Number: 6,117,137
[45] Date of Patent: Sep. 12, 2000

[54] OSTEOSYNTHESIS DEVICE

[75] Inventors: Henry Halm, Bissendorf-Wissingen; Bernd Schäfer, Göppingen, both of Germany

[73] Assignee: SCHAFER micomed GmbH, Goppingen, Germany

[21] Appl. No.: 09/299,621

[22] Filed: Apr. 27, 1999

[30] Foreign Application Priority Data

Apr. 27, 1998 [DE] Germany .......................... 198 18 765

[51] Int. Cl.[7] ............................................. A61B 17/58
[52] U.S. Cl. ................... 606/72; 606/73; 606/61
[58] Field of Search ................... 606/61, 69, 72, 606/73

[56] References Cited

U.S. PATENT DOCUMENTS

| | | | |
|---|---|---|---|
| 5,643,261 | 7/1997 | Schafer et al. | 606/61 |
| 5,738,685 | 4/1998 | Halm et al. | 606/61 |
| 5,961,517 | 10/1999 | Biedermann et al. | 606/61 |

*Primary Examiner*—Michael Buiz
*Assistant Examiner*—Daphna Shai
*Attorney, Agent, or Firm*—Jones, Tullar & Cooper, P.C.

[57] ABSTRACT

The present invention relates to an osteosynthesis device with a bone screw and a correction rod, in which the correction rod is placed in a bifurcated head of the bone screw and axially fixed. To that end, the bifurcated head has structure that prevent the longitudinal displacement of the correction rod.

12 Claims, 1 Drawing Sheet

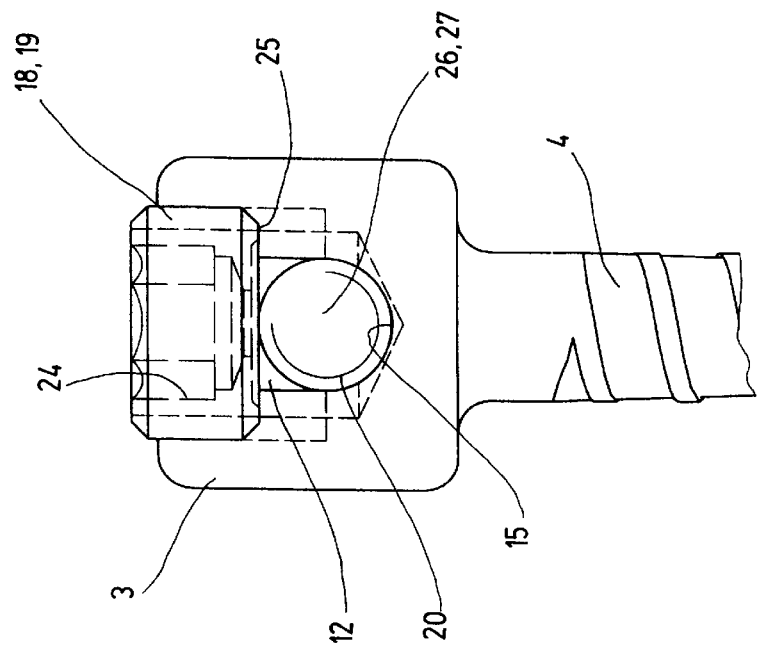
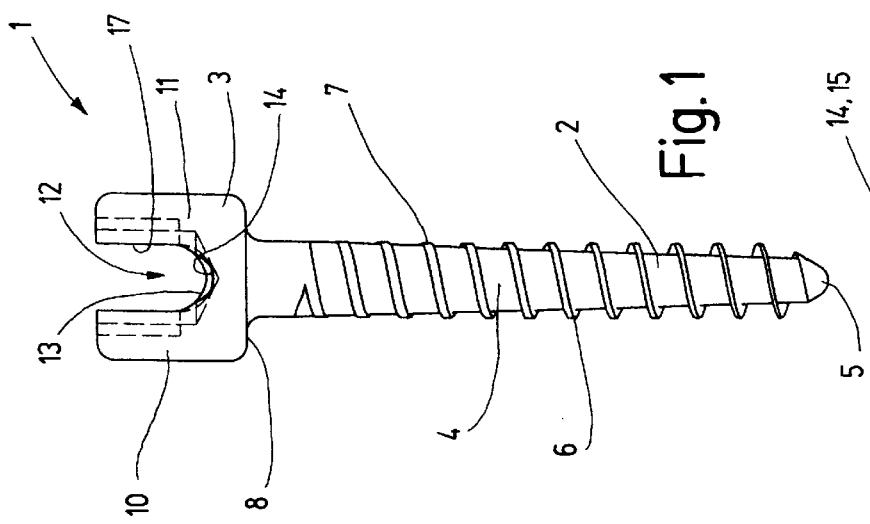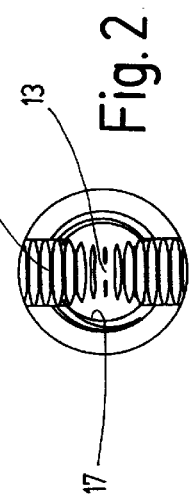

OSTEOSYNTHESIS DEVICE

FIELD OF THE INVENTION

The present invention relates to an osteosynthesis device, having a bone screw with a bifurcated head that has a groove, and a correction rod to be placed in the groove of the bifurcated head; the correction rod has a surface profile, the bifurcated head at the groove bottom has a surface profile, and is provided with means that fix the correction rod.

BACKGROUND OF THE INVENTION

From German Patent DE 43 16 542 C1, a bone screw is known with which a longitudinally grooved rod can be fixed in a manner secure against relative rotation. To that end, the bone screw has a bifurcated head, in whose groove the longitudinally grooved rod can be placed. The grooved bottom is itself provided with longitudinal grooves, which establish a positive connection with the rod. For fixing the rod, a cap nut is screwed onto the bifurcated head, and the rod is firmly clamped in the groove bottom with this nut. Because the rod is fixed to the bone screw in a manner secured against relative rotation, high correction forces or retention forces can be transmitted. However, to transmit forces oriented in the longitudinal direction of the rod, additional aids or additional rods are needed.

From German Patent DE 26 49 942 C2, a corrective implant is known in which such longitudinal forces can be introduced optimally into the bone screws via a threaded rod. Once again, the bone screw has a bifurcated head, in which the threaded rod is placed. The fixation of the threaded rod is done by means of two nuts, which are seated on the threaded rod and are screwed laterally partway into the bifurcated head. In this way, the threaded rod is fixed on the bone screw. It has proved to be a disadvantage in this known construction that fastening the threaded rod to the bifurcated head of the bone screw, and in particular screwing the nuts into the bifurcated head, is inconvenient and wastes time, since the nuts can be turned or tightened only with an engineer's wrench, and displacement of the threaded rod is possible only whenever the nut is spaced sufficiently far from the bifurcated head.

SUMMARY OF THE INVENTION

It is therefore an object of the present invention to embody a device of the type defined at the outset in such a way that the fixation of the correction rod to the bifurcated head of the bone screw can be done on the one hand securely and on the other in the shortest possible time.

According to the present invention, this object is attained in that the surface profiling of the groove bottom has means for the longitudinal displacement of the correction rod in the groove, and that the means fixing the correction rod is a screw means, which can be secured to the bifurcated head.

The substantial advantage of the osteosynthesis device of the present invention is considered to be that the groove bottom and in particular the profiling of the groove bottom has means that prevent a longitudinal displacement of the correction rod in the bifurcated head. The bifurcated head of the bone screw also has a screw means with which the correction rod is fixed in the groove bottom. By loosening this screw means, which can be done relatively simply and quickly, this fixation can be undone, so that recorrection or readjustment can be done. Merely by loosening the screw means that can be secured to the bifurcated head, that is, the screw means that is screwed to the bifurcated head, the correction rod is released so that it can be displaced into an arbitrary position, regardless of what position the screw means assumes if it has become loose.

Further advantages, characteristics and details of the present invention will become apparent from the ensuing description and claims.

The screw means may be embodied as a nut, in particular as a cap nut, which is screwed onto a male thread of the bifurcated head. In this way, as in German Patent DE 43 16 542 C1, the correction rod is optimally joined to the bone screw. The nut also offers the substantial advantage that it can be actuated with a single tool.

In another embodiment, the screw means is embodied as a grub screw and is screwed into a female thread of the bifurcated head. The grub screw is provided with a hexagonal socket, for instance, and can be actuated with a conventional hexagonal tool. The grub screw may be provided with a point or an annular cutting edge, which when the grub screw is tightened rests on the correction rod and digs into it and fixes the correction rod to the bifurcated head.

In a preferred exemplary embodiment, the correction rod is a threaded rod. The surface profiling has transverse grooves extending crosswise to the longitudinal axis of the correction rod. These transverse grooves correspond to the thread of the correction rod. In a preferred exemplary embodiment, the transverse grooves have a lesser depth than the thread of the correction rod. This has the substantial advantage that the possibility exists, in the tightening of the screw means, that the correction rod will be deformed plastically, or at least elastically, in the region of contact with the transverse grooves, and as a result security against an axial displacement is attained. Further optimization can be attained by providing that the transverse grooves have a pitch corresponding to the thread of the correction rod. In particular with a fine thread, this assures an optimal contact of the threaded rod with the transverse grooves.

In another embodiment of the present invention, the surface profiling of the rod and of the bottom of the bifurcated head is a fluted profile. Such a fluted or knurled profile has the advantage that both axial displacements and rotations are prevented.

In another exemplary embodiment, the correction rod has circumferential grooves. A displacement of this rod is prevented just as is that of a threaded rod. The correction rod can be sand-blasted or bombarded, so that it has a compacted surface and has a relatively high surface hardness.

Other embodiments provide embodying the correction rod as a rack, perforated rod, and so forth. The groove bottom has a profile suitable for the embodiment of the correction rod.

BRIEF DESCRIPTION OF THE DRAWINGS

A particularly preferred exemplary embodiment said be described below, with reference to the drawing. Shown in the drawing are:

FIG. 1, which is a side view of a preferred embodiment of the present invention;

FIG. 2, which is a plan view on the bifurcated head of the bone screw; and

FIG. 3, which is an enlarged view of the head of the bone screw with the threaded rod placed in it.

DESCRIPTION OF THE PREFERRED EMBODIMENTS

In FIG. 1, a bone screw is identified overall by reference numeral 1 and has a threaded shaft 2 and a bifurcated head 3. The threaded shaft 2 comprises a screw core 4 with a screw point 5 and a thread 6 surrounding the screw core 4. It can be seen that the screw core 4 widens conically from the screw point 5 toward the bifurcated head 3. The diameter of the thread 6, however, remains constant while conversely the width of the threaded cutting edge 7 increases from the screw point 5 toward the bifurcated head 3. The pitch of the thread 6, however, remains constant over the entire length of the threaded shaft 2. It can also be seen in FIG. 1 that the underside 8 of the bifurcated head 3 is embodied as flat, and in particular is rounded.

The bifurcated head 3 has two legs 10 and 11, between which a groove 12 is machined. The groove 12 has walls that open slightly in conical fashion. The bottom 13 of the groove 12 is provided with a surface profiling 14, as can be seen from FIG. 2. It can also be seen that the surface profiling is machined into the groove bottom 13 in the form of transverse grooves 15. The transverse grooves 15 are formed either by milling or hammering.

The upper end of the bifurcated head 3 is provided with a female thread 17, which extends over approximately half the height of the bifurcated head 3. A screw element 18, which is embodied as a grub screw 19, can be screwed into this female thread 17.

The grub screw 19 has a hexagonal socket 24 on its top side. On its underside, the grub screw 19 is provided with an annular cutting edge 25, which when the grub screw 19 is tightened presses against a correction rod 26. This correction rod 26 (FIG. 3) is embodied as a threaded rod 27, and the thread 20 corresponds to the transverse grooves 15 of the groove bottom 13.

If the correction rod 26, as shown in FIG. 3, is placed in the groove 12 of the bifurcated head 3, then the thread 20 engages the transverse grooves 15 positively. Next, the grub screw 19 is screwed on, and the annular cutting edge 25 digs into the adjacent thread 20. In this way, the correction rod 26 is secured against displacement via the thread 20 that engages the transverse grooves 15 and against rotation via the annular cutting edge 25 that digs into the thread 20. Torques are also introduced from the correction rod 26 directly into the screw core 4 via the positive connection with the transverse grooves 15.

What is claimed is:

1. An osteosynthesis device, comprising:
    a bone screw having a bifurcated head at one end defining a groove, said groove having a bottom surface including surface profiling;
    a correction rod received in said groove, said correction rod including surface profiling; and
    screw means secured to said bifurcated head for fixing said correction rod to said bone screw,
    wherein said surface profiling of said bottom surface has means for inhibiting the longitudinal displacement of said correction rod in said groove.

2. The osteosynthesis device of claim 1, wherein said screw means comprises a nut, and wherein said bifurcated head has a male thread which is engaged by said nut.

3. The osteosynthesis device of claim 2, wherein said nut comprises a cap nut.

4. The osteosynthesis device of claim 1, wherein said screw means comprises a grub screw, and wherein said bifurcated head has a female thread which is engaged by said nut.

5. The osteosynthesis device of claim 1, wherein said surface profiling of said bottom surface comprises a fluted profile.

6. The osteosynthesis device of claim 1, wherein said correction rod includes circumferential grooves.

7. The osteosynthesis device of claim 1, wherein said correction rod is sand-blasted.

8. The osteosynthesis device of claim 1, wherein said correction rod is bombarded.

9. An osteosynthesis device, comprising:
    a bone screw having a bifurcated head at one end defining a groove, said groove having a bottom surface including surface profiling;
    a threaded correction rod received in said groove, said threaded correction rod defining a longitudinal axis and including surface profiling which includes transverse grooves extending crosswise to said longitudinal axis; and
    screw means secured to said bifurcated head for fixing said correction rod to said bone screw,
    wherein said surface profiling of said bottom surface has means for inhibiting the longitudinal displacement of said correction rod in said groove.

10. The osteosynthesis device of claim 9, wherein said transverse grooves correspond to the thread of said correction rod.

11. The osteosynthesis device of claim 10, wherein said transverse grooves have a lesser depth than the thread of said correction rod.

12. The osteosynthesis device of claim 10, wherein said transverse grooves have a pitch corresponding to that of threads of said correction rod.

* * * * *